United States Patent [19]

Collier

[11] Patent Number: 4,932,533
[45] Date of Patent: Jun. 12, 1990

[54] THERMAL-STABILIZED CONTAINER

[75] Inventor: Charles A. Collier, Bellevue, Wash.

[73] Assignee: Allpak Container, Inc., Tukwila, Wash.

[21] Appl. No.: 309,391

[22] Filed: Feb. 10, 1989

[51] Int. Cl.$^5$ .............................................. B65D 71/00
[52] U.S. Cl. ................................. 206/569; 206/443; 206/370; 206/562; 211/74
[58] Field of Search ............... 206/443, 486, 490, 521, 206/562, 569, 570, 815, 305, 370; 211/71, 74; 312/236

[56] References Cited

U.S. PATENT DOCUMENTS

| | | | |
|---|---|---|---|
| 1,644,830 | 10/1927 | Henderson | 206/370 |
| 1,680,804 | 8/1928 | Remley | 206/370 |
| 2,062,973 | 12/1936 | Gluckstein | 206/370 |
| 2,292,626 | 8/1942 | Ferguson | 206/210 |
| 3,175,695 | 3/1965 | Goodman et al. | 211/74 |
| 3,300,055 | 1/1967 | Rohr | 211/74 |
| 3,602,371 | 8/1971 | Weiner | 206/443 |
| 3,647,105 | 3/1972 | Keeslar | 206/443 |
| 4,057,148 | 11/1977 | Meyer et al. | 206/443 |
| 4,240,547 | 12/1980 | Taylor | 206/443 |
| 4,411,868 | 10/1983 | Noack | 211/71 |
| 4,501,360 | 2/1985 | Levy et al. | 206/443 |
| 4,573,581 | 3/1986 | Galloway et al. | 206/570 |
| 4,826,003 | 5/1989 | Levy | 206/443 |

Primary Examiner—David T. Fidei
Attorney, Agent, or Firm—Christensen, O'Connor, Johnson & Kindness

[57] ABSTRACT

A thermal-stabilized container (10) for protecting fragile objects stored in the container (10) and maintaining temperature-sensitive material in the objects within a predetermined temperature range for a predetermined period of time. The container (10) includes an outer shell (12), an inner carton (14), and a lid (16). Test tubes (18) having temperature-sensitive cultures (52) stored therein are firmly held within openings (30) in the carton (14). The carton (14) is slidably received within an interior (42) of the outer shell (12). Disposable heat sources (58) are activated and stored within cavities (56) formed in the end walls (36) of the outer shell (12). The tubes (18) are inclined at an angle with respect to the horizontal axis to provide greater surface contact between the cultures (52) and gases (54) in the tubes (18).

14 Claims, 2 Drawing Sheets

THERMAL-STABILIZED CONTAINER

TECHNICAL FIELD

The present invention is directed to shipping containers and, more particularly, to a temperature stabilizing shipping container for protecting fragile objects stored in the container and maintaining temperature-sensitive material in the objects within a predetermined temperature range for a predetermined period of time.

BACKGROUND OF THE INVENTION

The transportation of fragile, temperature-sensitive materials and, in particular, cultures stored in test tubes, through the normal shipping channels poses several unique problems. First, the test tubes, must be firmly held in place in a container to prevent movement and damaging contact between the test tubes. In addition, the test tubes must be sufficiently cushioned in protective material to resist breakage from crushing or rough handling.

The protective material must not only cushion the fragile test tubes, but it must also be thermally insulative to resist adverse temperature changes from outside or ambient temperatures. Typically, when cultures are shipped in test tubes, no heat source is provided to maintain the cultures in a living state other than the mass within the cultures. Over a period of time the cultures will be damaged or destroyed if not provided with sufficient heat. The cultures may also be adversely affected when subjected to very high temperatures. This frequently occurs when containers are exposed to adverse environmental conditions, such as when sitting in trucks, on an airport tarmac, etc. Consequently, it is desirable to provide a shipping container that will maintain the cultures within a predetermined temperature range to ensure they will be in a viable condition when they arrive at their destination. It is also desirable to provide a heat source or heat sink in the container that is lightweight, compact, and reusable or disposable.

Finally, when test tubes containing cultures are shipped, it is desirable to have the test tubes oriented at an angle from the horizontal to permit greater surface area contact between the gas and the liquid in the test tube to increase the growth of the cultures. Therefore, the shipping container should be configured to firmly hold the test tubes at an angle from the horizontal during shipping.

SUMMARY OF THE INVENTION

A thermal-stabilized container for shipping temperature-sensitive materials stored in fragile objects is provided. The container includes a carton having a plurality of openings formed therein for firmly holding a plurality of fragile objects, such as glass test tubes, in spaced relationship to one another. Preferably, the carton is receivable within an outer shell for greater insulation and cushioning. The outer shell has at least one wall, a bottom, and an open top. One or more cavities are formed in the outer shell to store one or more temperature control devices in spaced relationship to the fragile objects to maintain the temperature-sensitive material within a predetermined temperature range for a predetermined period of time. The container further includes a lid sized and shaped to cover the open top to insulate the temperature-sensitive material and retain the fragile objects therein.

In accordance with another aspect of the present invention, the container further includes one or more lightweight, self-contained temperature control devices stored in one or more cavities. Preferably, the one or more temperature control devices are heat sources or heat sinks that are either disposable or reusable.

In accordance with another aspect of the present invention, the predetermined temperature is in the range of 59° F. to 99° F. In addition, the predetermined period of time is in the range of 20 hours to 28 hours.

In accordance with yet another aspect of the present invention, the carton is configured to hold the fragile objects at a predetermined angle with respect to a horizontal axis. The predetermined angle is in the range of 5° to 10°, with a preferable value of 7°.

In accordance with yet another aspect of the present invention, the outer shell, carton, and lid are formed of lightweight, rigid, thermally insulative material, preferably molded expanded polystyrene.

As will be readily appreciated from the foregoing description, the present invention provides a lightweight, sturdy shipping container that includes one or more temperature control devices for maintaining the material stored in the container within a desired temperature range for the period of time it takes to ship the container to its destination. The self-contained heat sources or heat sinks can be quickly replaced and the container used again without delay. In applications where cultures are shipped in test tubes, the orientation of the test tubes at a predetermined angle facilitates greater growth of cultures because of increased surface area exposure between the liquid and gas in the test tubes. The container uses molded expanded polystyrene, which is light in weight, a good insulator, and a cost-efficient material that is easy to fabricate. In addition, this material has some flexibility to absorbed shock and bend, and it allows easy insertion and removal of test tubes while at the same time providing a firm grip on the test tubes to retain them in the carton.

BRIEF DESCRIPTION OF THE DRAWINGS

The foregoing and other features and advantages of the present invention will become better understood from the following description of the preferred embodiment of the invention when taken in conjunction with the following drawings, wherein.

DETAILED DESCRIPTION OF THE PREFERRED EMBODIMENT

Figure 1:
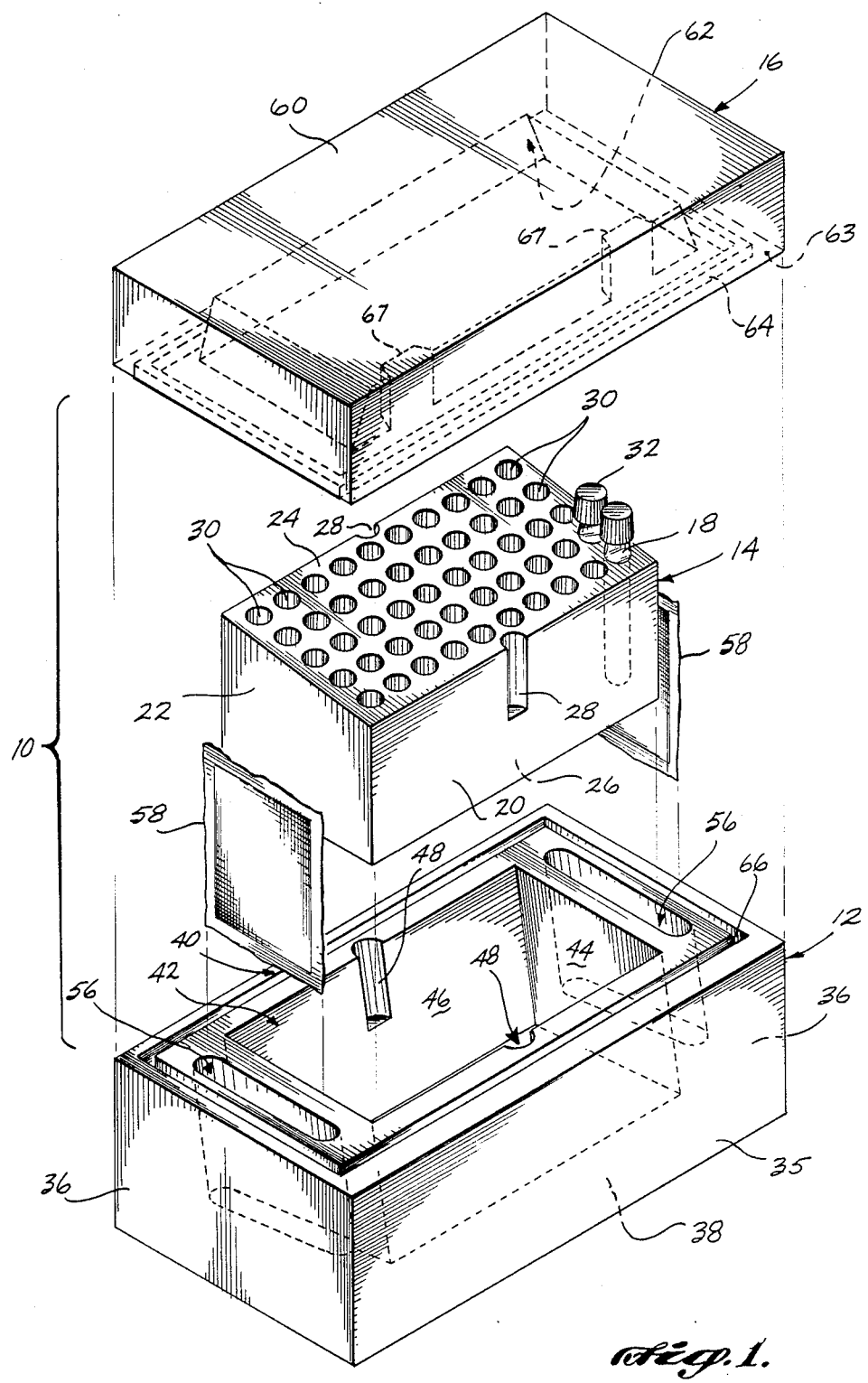
FIG. 1 is an exploded, isometric view of a thermal-stabilized container formed in accordance with the present invention.
Figure 2:
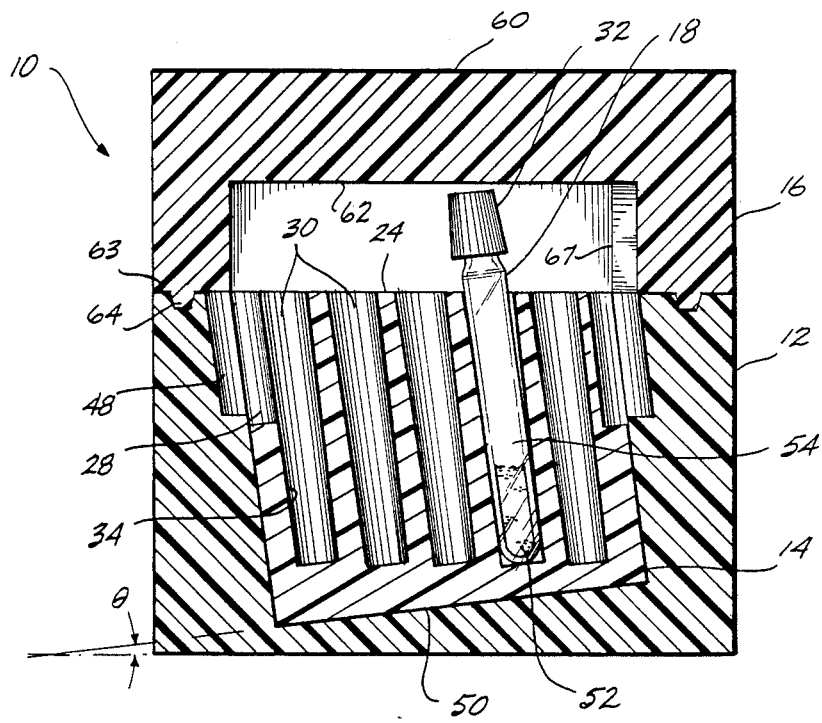
FIG. 2 is a cross section view of the assembled thermal-stabilized container of FIG. 1.

A representative embodiment of a thermal-stabilized container 10 formed in accordance with the present invention is illustrated in FIGS. 1 and 2. The container 10 is comprised of an outer shell 12, an inner carton 14, and a lid 16. Representative test tubes 18 are illustrated to show their retention in the container 10. Although the container is shown having a rectangular shape, it is to be understood that other shapes, such as a cylinder or cube, may be used without departing from the spirit and scope of the invention.

The inner carton 14 is of a rectangular shape having two long sides 20, two ends 22, a top surface 24, and a bottom surface 26. The top surface 24 slopes downward from one side 20 to the other long side 20, as is shown more clearly in FIG. 2. A channel 28 having a semicircular cross-sectional shape is formed in the surface at the center of each side 20, extending from the top surface 24 to midway down the surface of each side 20.

A plurality of openings 30 are formed in the carton 14 that open to the top surface 24. The openings 30 are sized and shaped to receive the glass test tubes 18. In the representative embodiment depicted in FIGS. 1 and 2, the walls 34 of the openings are formed to taper downward from the top surface 24 at approximately a 1° angle. The openings 30 have an inside diameter sized to firmly grip the test tubes 18 when they are fully inserted into the carton 14. The test tubes 18 have caps 32 that are sized larger than the openings 30, and they remain visible above the top surface 24 of the carton 14.

The outer shell 12 is formed to have two side walls 35, two end walls 36, a bottom 38, and open top 40 that provide access to an open interior 42. The open interior 42 is bounded by two pairs of opposed interior surfaces 44 and 46. The longer pair of interior surfaces 46 has channels 48 formed therein with semicircular cross-sectional shapes that extend from the top 40 of the outer shell 12 to midway down the surface 46. The open interior 42 is sized and shaped to slidably receive the inner carton 14. When the inner carton 14 is received within the outer shell 12, the channels 28 in the inner carton 14 will align with the channels 48 in the outer shell to provide an opening for a handler to grasp the inner carton 14 to insert and remove it from the outer shell 12.

As shown in FIG. 2, the open interior 42 of the outer shell 12 has an inclined bottom 50 that diverges from the horizontal bottom 38 of the outer shell 12 at a predetermined angle that is in the range of 5° to 10°, and preferably has a value of 7°, as indicated by the angle $\theta$. The angle matches the slope of the top surface 24 of the inner carton 14, such that when the inner carton 14 is slidably received within the outer shell 12, the top surface 24 will be flush with the open top 40 of the outer shell 12. In addition, the test tubes 18 will be held at the angle $\theta$ so that temperature-sensitive cultures 52 stored therein will have greater surface area contact with gases 54 in the tubes 18.

The two opposed end walls 46 each have a cavity 56 formed therein. The cavity is sized to receive a heat source or heat sink to provide temperature control of the cultures 52 stored within the container 10. In the representative embodiment depicted in FIG. 1, a heat source 58 is inserted in each of the cavities 56. In this case, the heat source is a combination of iron, water, cellulose, vermiculite, activated carbon, and salt contained within an air-permeable sack. When the ingredients in the sack come into contact with the air, the chemical reaction between the contents and the air generates heat. The packets are described in U.S. Pat. No. 3,976,049, and can be obtained from John Wagner Associates, Inc., in Concord, California. The packets generate heat at a temperature of between 140° F. and 160° F. for a period of time ranging from 20 hours to 28 hours.

The lid 16 is sized and shaped to cover the open top 40 of the outer shell 12. The lid 16 has a top surface 60 and a bottom surface 62, with a lip 64 protruding downward from around the perimeter 63 of the lid 16. A corresponding channel 66 is formed in the top surfaces of the side walls 35 and end walls 36 of the outer shell 12. The channel 66 is sized and shaped to snugly receive the lip 64. In this manner the lid 16 is firmly held in place on the outer shell 12. As shown in FIG. 2, when the lid 16 is placed on the outer shell 12, protrusions 67 on the bottom surface 62 of the lid 16 will bear against the top surface 24 of the inner carton 14 to assist in holding the inner carton 14 in place in the outer shell 12.

In use, the removable inner carton 14 may be separately used to store test tubes 18 in a laboratory. When it is desired to ship the test tubes 18, the inner carton 14 is grasped with one or more fingers in the channels 28 and placed within the outer shell 12. The spaces provided by the aligned channels 28 and 48 allow a handler to easily insert and remove the inner carton 14 from the outer shell 12. The heat sources 58 are then activated by exposure to the air and placed within the cavities 56 to generate heat and the lid 16 is then placed over the open top 40 of the outer shell 12. The lid 16 may be retained in place with straps, or, alternatively, the assembled container 10 can be placed within another container for further protection during shipping.

Ideally, the outer shell 12, the inner carton 14, and the lid 16 are constructed of a lightweight, substantially rigid, thermally insulative material such as molded expanded polystyrene. It has been found that expanded polystyrene of a density of 1.0 to 1.2 pounds per cubic foot provides the best insulation for the lightest weight and cost. In addition, outer shell wall thicknesses of 1.25 to 1.75 inches have been found to be suitably thick to provide protection and insulation without unduly increasing the weight and the cost for adequate protection against environmental temperature above 30° F. and below 120° F., for a period of approximately four to six hours. It is to be understood, however, that other materials such as polyethylene, or other forms of solid foam material that are good insulators and easy to mold may be used.

It is also to be understood that, while a preferred embodiment of the invention has been illustrated and described, various changes can be made therein without departing from the spirit and scope of the invention. For instance, the heat sources 58 may be replaced with a heat sink that maintains the temperature of the temperature-sensitive material below the temperature of the ambient air. Such a heat seal may be formed from ice, dry ice, frozen metal, etc. It is to be further understood that the range of temperatures and the length of time at which the temperature is maintained can be varied according to the type of temperature control device selected to be stored in the cavities 56. Furthermore, the angle at which the test tubes are held may also be varied to suit the needs of a particular application. Finally, while the cavities 56 are shown being formed in the end walls 56 of the outer shell 12, it is to be understood that these cavities may also be formed in the side walls of the outer shell, or in the inner carton 14 itself. Furthermore, the temperature control devices may also be stored below or above the inner carton 14, such as in the lid 16 or in a cavity formed in the inclined bottom 50 of the open interior 42 in the outer shell 12. It is also to be appreciated that, while a three-piece configuration has been shown and described, the invention can be practiced in a two-piece configuration wherein the inner carton 14 is integrally formed with the outer shell 12. The advantage of the three-piece construction is to permit the storage of test tubes in the more space-efficient inner carton 14 until it is desired to ship them. In addition, the lid 16 may be hingedly formed or attached to the outer shell 12.

The embodiments of the invention in which an exclusive property or privilege is claimed are defined as follows:

1. A thermal-stabilized container for shipping fragile, temperature sensitive objects, the container comprising:
   (a) one or more temperature control devices including a disposable heat source;
   (b) a carton formed of rigid, lightweight, thermal insulating material for holding one or more fragile objects, the carton having one or more openings for firmly holding the one or more objects in spaced relationship to one another, the carton further including means for storing the one or more self-contained temperature control devices in spaced relationship to the one or more objects to maintain the one or more objects at a temperature ranging between 59° F. to 99° F. for a predetermined period of time, the carton further including one or more walls, a bottom, and an open top; and
   (c) means for enclosing the one or more objects and the one or more temperature control devices in the carton, the enclosing means including a lid for covering the open top of the carton.

2. The container of claim 1, wherein the predetermined period of time is in the range of 20 hours to 28 hours.

3. The container of claim 2, wherein said carton is configured to hold the one or more objects at a predetermined angle from a horizontal axis.

4. The container of claim 3, wherein the predetermined angle is in the range of 5° to 10°.

5. The container of claim 3, wherein the predetermined angle is preferably 7°.

6. A thermal-stabilized container for shipping temperature-sensitive materials stored in fragile objects, the container comprising:
   (a) an outer shell having at least one wall, a bottom, and an open top, said outer shell being constructed of a rigid, lightweight, thermal insulating material;
   (b) an inner carton sized and shaped to be stored within said outer shell, said inner carton having one or more openings formed therein for firmly holding one or more fragile objects in spaced relationship to one another, said inner carton being configured to hold said one or more fragile objects at a predetermined angle from a horizontal axis, said inner carton being further constructed of a rigid, lightweight thermal insulating material;
   (c) means for storing one or more lightweight, self-contained temperature control devices in spaced relationship to said one or more fragile objects such that temperature-sensitive material stored in said one or more fragile objects will be maintained within a predetermined temperature range for the predetermined period of time; and
   (d) a lid sized and shaped to cover the open top of the outer shell, said lid being constructed of a rigid, lightweight thermal insulating material.

7. The container of claim 5, wherein said storing means comprises one or more cavities formed in said outer shell.

8. The container of claim 7, further comprising a disposable heat source sized to be stored in said one or more cavities.

9. The container of claim 7, further comprising a disposable heat sink sized to be stored in said one or more cavities.

10. The container of claim 7, further including a reusable heat source sized to be stored in said one or more cavities.

11. The container of claim 7, further comprising a reusable heat sink sized to be stored in said one or more cavities.

12. The container of claim 7, wherein said predetermined temperature is in the range of 59° F. to 99° F.

13. The container of claim 7, wherein said predetermined angle is in the range of 5° to 10°.

14. The container of claim 7, wherein said rigid, lightweight, thermal insulating material is molded expanded polystyrene.

* * * * *

UNITED STATES PATENT AND TRADEMARK OFFICE
CERTIFICATE OF CORRECTION

PATENT NO. : 4,932,533
DATED : June 12, 1990
INVENTOR(S) : Charles A. Collier

It is certified that error appears in the above-identified patent and that said Letters Patent is hereby corrected as shown below:

| Column | Line | |
|---|---|---|
| 2 | 36 | "absorbed" should be --absorb-- |
| 3 | 44 | "46" should be --36-- |
| 4 | 30 | "temperature" should be --temperatures-- |
| 5 | 5 | "temperature sensitive" should be --temperature-sensitive-- |
| 6 | 18 | "5" should be --6-- |

Signed and Sealed this

Third Day of March, 1992

Attest:

HARRY F. MANBECK, JR.

*Attesting Officer*     *Commissioner of Patents and Trademarks*